US00PP35768P2

(12) United States Plant Patent
Van Dijk

(10) Patent No.: US PP35,768 P2
(45) Date of Patent: Apr. 23, 2024

(54) ***ANTHURIUM* PLANT NAMED 'AN2443227'**

(50) Latin Name: ***Anthurium andraeanum* L.**
Varietal Denomination: AN2443227

(71) Applicant: ANTHURA B.V., Bleiswijk (NL)

(72) Inventor: Jan Van Dijk, Bleiswijk (NL)

(73) Assignee: Anthura B.V., Bleiswijk (NL)

( * ) Notice: Subject to any disclaimer, the term of this patent is extended or adjusted under 35 U.S.C. 154(b) by 0 days.

(21) Appl. No.: 18/445,521

(22) Filed: Sep. 21, 2023

(51) Int. Cl.
*A01H 6/00* (2018.01)
*A01H 5/02* (2018.01)

(52) U.S. Cl.
USPC ..... Plt./365

(58) Field of Classification Search
USPC ..... Plt./365
CPC ..... A01H 6/00; A01H 5/02
See application file for complete search history.

*Primary Examiner* — Keith O. Robinson
(74) *Attorney, Agent, or Firm* — Jondle & Associates, P.C.

(57) ABSTRACT

A new *Anthurium* plant named 'AN2443227' particularly distinguished by having strongly blistered, strongly glossy, green with red venation and red tips, oblong-cordate and durable spathes that retain the original color for a very long period of time, weakly glossy, dark green and narrowly long cordate, durable leaves, pink spadices with reddish-brown tips, early and rich flowering continuously throughout the year, and a plant height of 60.0 cm to 70.0 cm is disclosed.

3 Drawing Sheets

Genus and species: *Anthurium andraeanum* L.
Variety denomination: 'AN2443227'.

BACKGROUND OF THE NEW PLANT

The present invention comprises a new and distinct variety of *Anthurium*, botanically known as *Anthurium andraeanum* L., and hereinafter referred to by the variety name 'AN2443227'. The new *Anthurium* plant is a product of a planned breeding program conducted by the inventor in Bleiswijk, the Netherlands. The objective of this breeding program was to create a new cut flower plant with a height of 60.0 cm to 70.0 cm having strongly blistered, strongly glossy, green with a red venation and red tips, oblong-cordate, durable spathes.

The new variety originated from a cross-pollination made in November 2006 in Bleiswijk, the Netherlands. The female parent was a green *Anthurium* pot plant designated '06-008398-0002' (unpatented), and the male parent was a white *Anthurium* pot plant designated '03-006204-0001' (unpatented).

A single plant was selected from the progeny of the stated cross in May 2009. Asexual reproduction of the new variety by tissue culture in 2017 in Bleiswijk, the Netherlands, has demonstrated that the new variety reproduces true to type with all of the characteristics, as herein described, firmly fixed and retained through successive generations.

Community Plant Variety Rights for this variety have been applied for in the European Union on Nov. 23, 2022 (Application no. 2022/2644), by Applicant who obtained the subject matter disclosed directly from the inventor. 'AN2443227' has not been made publicly available or sold anywhere in the world prior to the effective filing date of this application with the exception of sales or disclosures made one year or less before the effective filing date of this claimed invention by Applicant who obtained 'AN2443227' directly from the inventor.

SUMMARY OF THE INVENTION

The following are the most outstanding and distinguishing characteristics of this new variety when grown under normal horticultural practices in Bleiswijk, the Netherlands:

1) Strongly blistered, strongly glossy, green with a red venation and red tips, oblong-cordate spathes;
2) Pink spadices with reddish-brown tips;
3) Weakly glossy, dark green, narrowly long cordate leaves; and
4) Spathes: relative position of lobes is adpressed.

DESCRIPTION OF THE PHOTOGRAPHS

This new *Anthurium* plant is illustrated by the accompanying photographs which show the overall plant habit including blooms, buds, and foliage of the plant; the colors shown are as true as can be reasonably obtained by conventional photographic procedures. The photographs are of a 60-week-old plant grown in a greenhouse in Bleiswijk, the Netherlands, in May 2023. Colors in the photographs may differ from the color values cited in the detailed botanical description, which accurately describes the actual colors of the new variety.

DESCRIPTION OF THE NEW VARIETY

Figure 1:
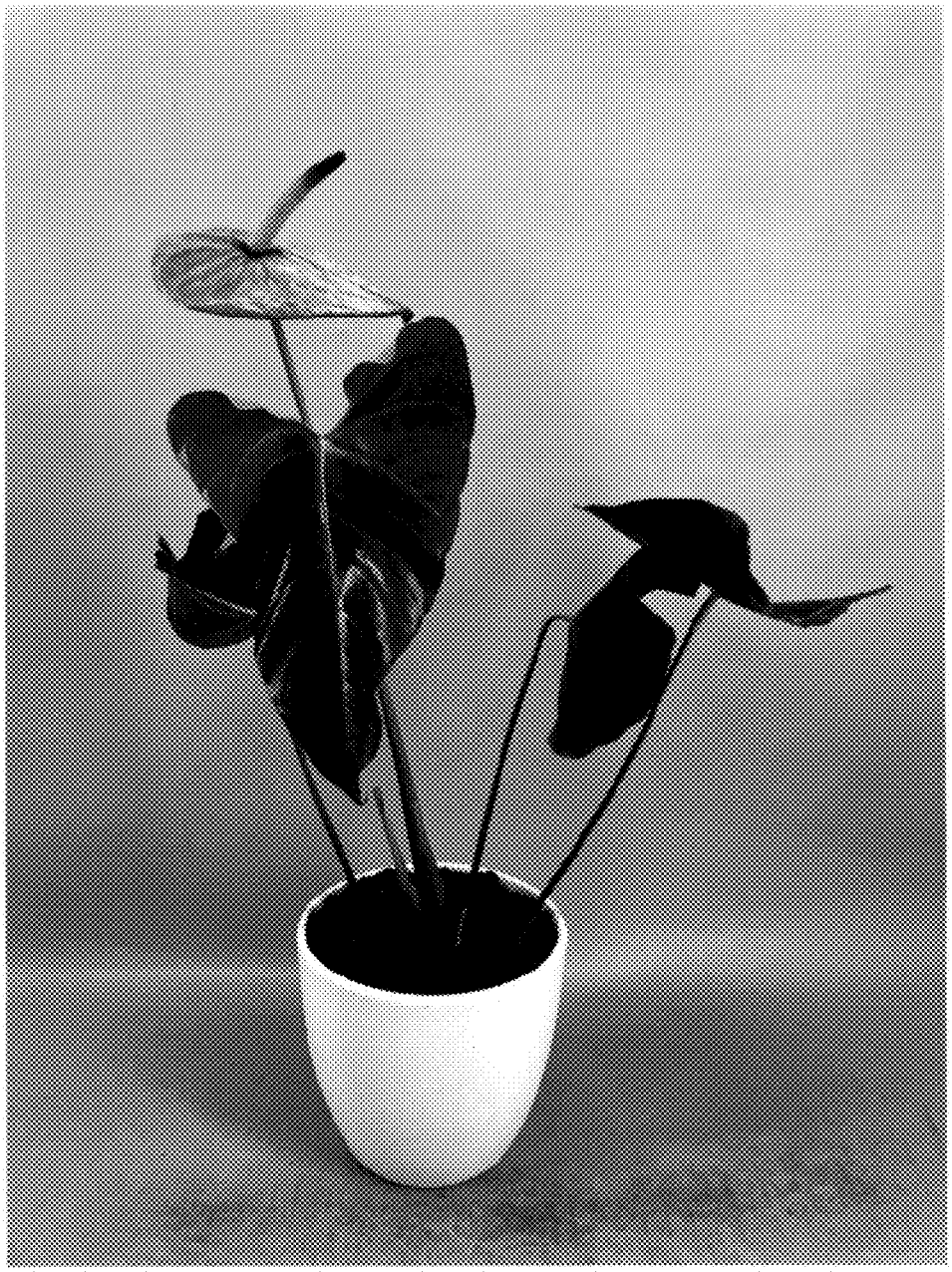
FIG. 1 shows the overall plant habit, including blooms, buds, and foliage.
Figure 2:
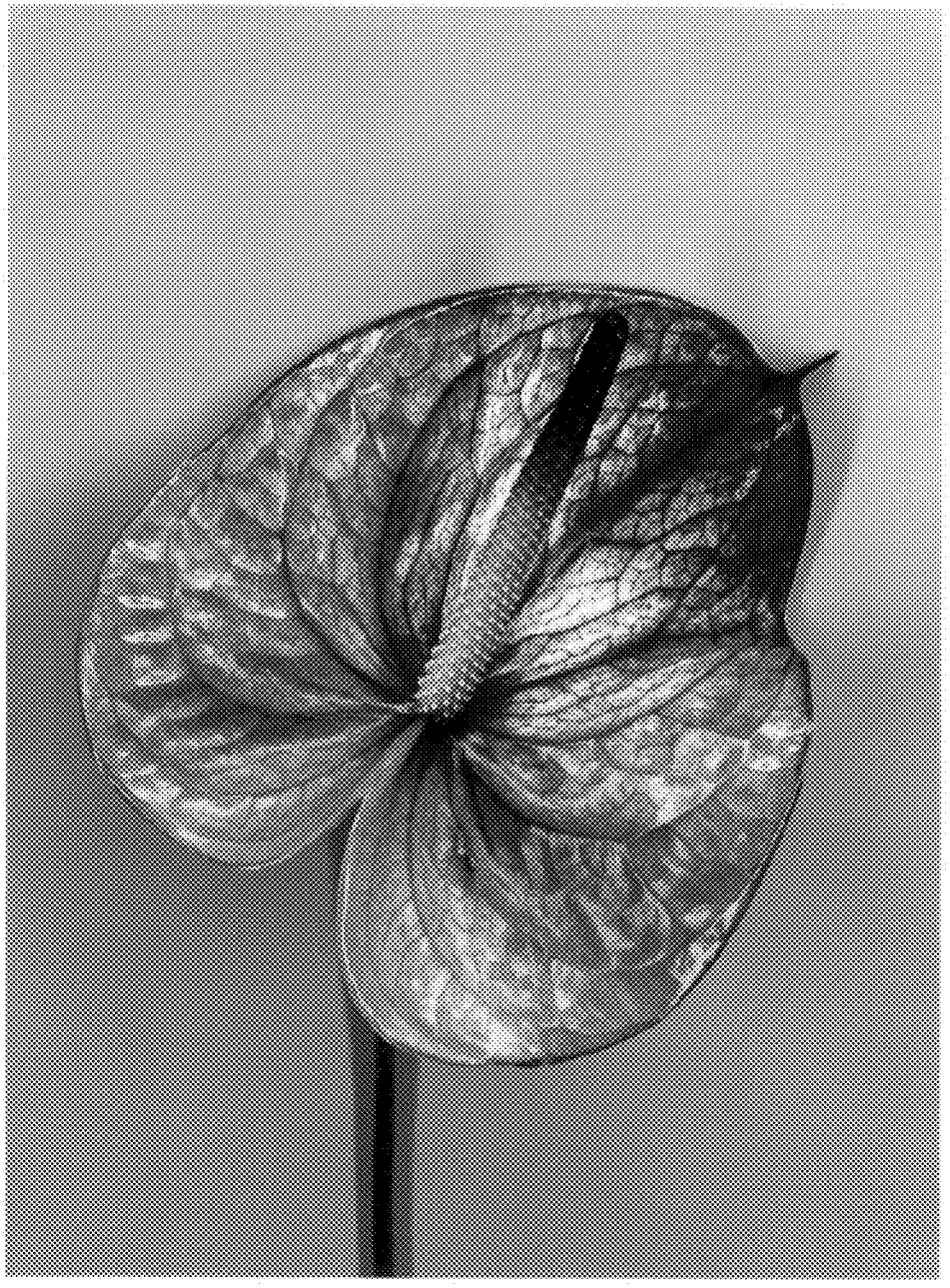
FIG. 2 shows a close-up of the mature spathe.
Figure 3:
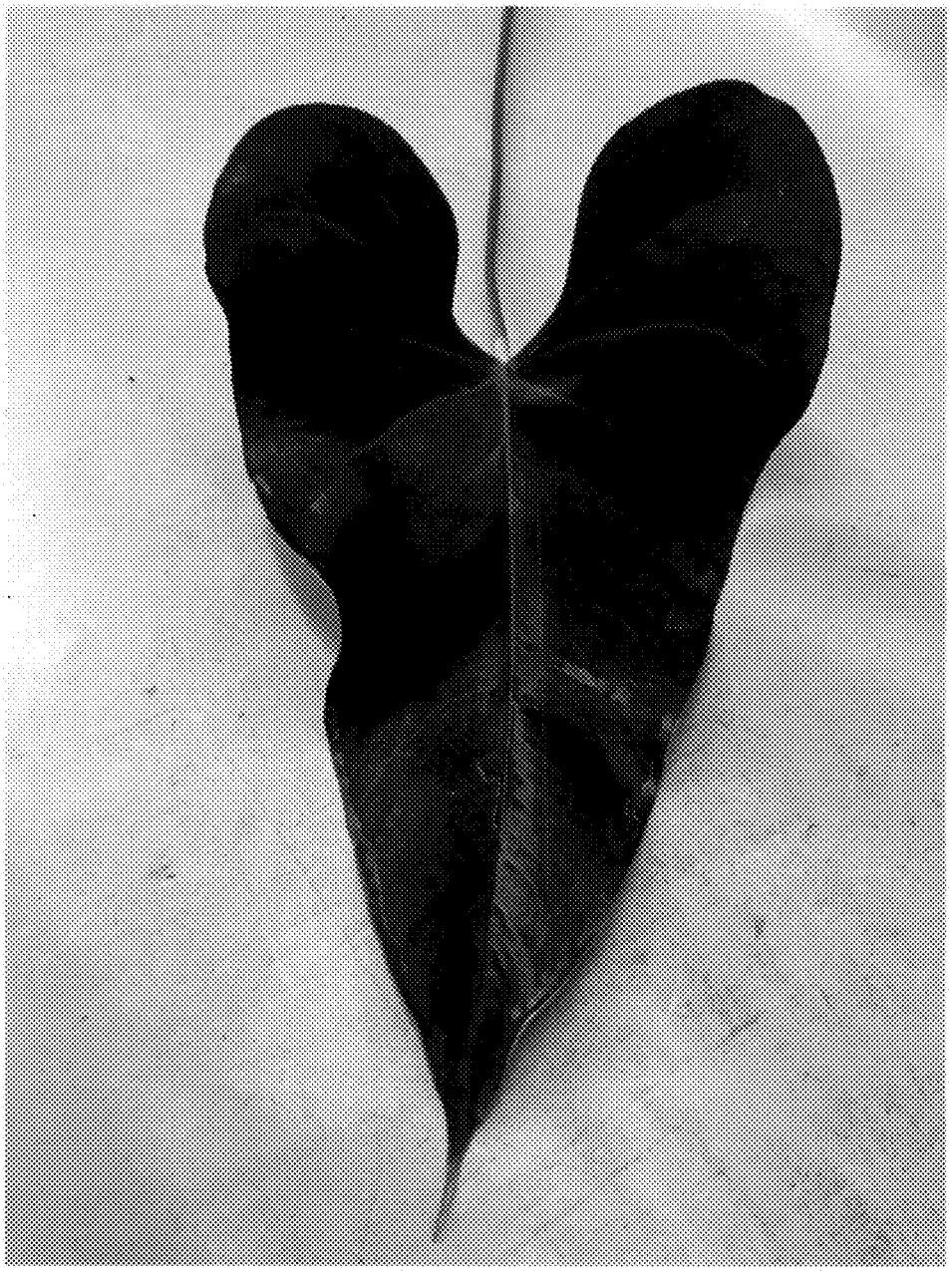
FIG. 3 shows a close-up of the upper leaf blade surface.

The following detailed description sets forth the distinctive characteristics of 'AN2443227'. The data which define these characteristics were collected from asexual reproductions carried out in Bleiswijk, the Netherlands. The plant history was taken on 60-week-old plants which were planted from tissue culture in 17-centimeter (diameter) pots and grown in a glass greenhouse between 19° C. and 24° C.

Observations were made in May 2023. Color readings were taken under 5000 lux natural light in the greenhouse. Color references are primarily to The R.H.S. Colour Chart of The Royal Horticultural Society of London (R.H.S.) (2015).

DETAILED BOTANICAL DESCRIPTION

Classification:

*Family*.—Araceae.

*Botanical*.—*Anthurium andraeanum* L.

*Common name*.—*Anthurium*.

*Denomination*.—'AN2443227'.

Parentage:

*Female parent*.—*Anthurium* plant '06-008398-0002' (unpatented).

*Male parent*.—*Anthurium* plant '03-006204-0001' (unpatented).

Plant:

*Propagation*.—Tissue culture.

*Root description*.—Fleshy-creamy (RHS 160B) colored roots and small, hairy lateral roots having small, light yellow-green (RHS 154D) colored root tips.

*Time to produce a flowering plant*.—55 to 66 weeks after planting in a 17-cm (diameter) pot.

*Growth habit*.—Upright.

*Height* (*measured from soil, including inflorescence*).—60.0 cm to 70.0 cm.

*Width* (*measured from leaf tips*).—45.0 cm to 55.0 cm.

Leaves:

*Immature leaves*.—Length: 30.0 cm to 33.0 cm. Width: 16.0 cm to 18.0 cm. Color: Upper surface: Green (RHS 146A) with red tips (RHS 46A). Lower surface: Green (RHS 146B). Texture (both upper and lower surfaces): Leathery, soft, thin, and strongly glossy.

*Mature leaves*.—Length (fully expanded): 34.0 cm to 37.0 cm. Width: 18.0 cm to 20.0 cm. Shape: Narrowly long cordate. Apex: Abruptly acuminate. Base: Cordate. Leaf blade angle with the petiole: Between 95 degrees and 110 degrees. Leaf margin: Entire. Color: Upper surface: Green (RHS 147A) with red (RHS 181B) tips at the base. Lower surface: Green (RHS 146A). Texture (both upper and lower surfaces): Leathery, thick, smooth, and weakly glossy. Venation: Pinnate veining; the mid-vein and primary veins (the veins which radiate out from junction of petiole and leaf) protrude at the underside of the leaf blade. Venation color: Upper surface: Green (RHS 144B). Lower surface: Green (RHS 144C).

*Lobes*.—Present. Arrangement: Leaf blade has two lobes extending past the petiole. The lobes are free. Length of lobes of mature leaf blades: 8.5 cm to 9.5 cm. Width of lobes of mature leaf blades: 8.5 cm to 9.0 cm. Distance from petiole/leaf junction to highest point on lobes of mature leaf blades: 5.0 cm to 6.0 cm.

*Petiole*.—Cross-section: Round. Diameter: 0.4 cm to 0.5 cm. Length: 36.0 cm to 38.0 cm for a mature leaf size. Color: Mature leaf: Green (RHS 144A) with a touch of red (RHS 175B) on the front side. Immature leaf: Green (RHS 144B). Cataphyll color surrounding the petiole: Outside: Green (RHS 144A) and reddish-orange (RHS 182B) on one side. Inside: Light green (RHS 145C).

*Geniculum*.—Length: 2.5 cm to 3.0 cm. Width: 0.5 cm to 0.6 cm. Color: Green (RHS 144B).

Inflorescence:

*Arrangement*.—Single.

*Flowering habit* (*length of flowering season*).—Continuous.

*Number of inflorescences per plant*.—5 to 7 flowers in a period of one year.

*Fragrance*.—Absent.

*Longevity of inflorescence on plant*.—40 to 45 days.

Spathe:

*Buds*.—The spathe is tightly rolled around the spadix and extrudes from the peduncle sheath.

*Arrangement*.—Spathe angle with the peduncle is between 100 degrees and 120 degrees; the spathe stands on a wiry peduncle about 10.0 cm to 15.0 cm above the foliage.

*Shape*.—Oblong-cordate.

*Apex*.—Abruptly acuminate.

*Base*.—Cordate.

*Texture*.—Strongly blistered and strongly glossy.

*Margin*.—Undulated.

*Size*.—Length: 17.0 cm to 18.0 cm. Width: 15.0 cm to 16.0 cm.

*Lobes*.—Present. Arrangement: The spathe has two lobes extending past the peduncle. The lobes are adpressed. Length: 5.0 cm to 5.5 cm. Width: 8.0 cm to 8.5 cm.

*Color*.—Just fully open: Upper surface: Green (RHS 144B) with red venation and tips (RHS 46A). Lower surface: Green (RHS 144C).

Peduncle:

*Shape*.—Erect.

*Cross-section*.—Round.

*Length*.—46.0 cm to 51.0 cm.

*Diameter*.—0.6 cm to 0.7 cm.

*Color*.—Green (RHS 144B) with a touch of red (RHS 182B).

Flowering time:

*General*.—One small, rooted, untreated tissue culture plant of 4.0 cm tall will flower for the first time, depending on the season, after 30 to 35 weeks.

Spadix:

*Size*.—Length: 8.0 cm to 9.0 cm (depending on flower size). Width (at apex): 0.8 cm to 0.9 cm. Width (at base): 1.0 cm to 1.2 cm.

*Shape*.—Columnar.

*Angle of spadix tip with peduncle*.—130 degrees to 150 degrees.

*Texture*.—When the spathe is unfurling, the spadix is smooth. When the spadix matures, small stigmata protrude. The stigmata are evenly distributed around the spadix. The spadix matures from base to top, slowly giving the spadix a somewhat rough appearance.

*Color*.—Immature: Reddish-brown (RHS 200B). Mature: Pink (RHS 34D). Ages to: Olive-brown (RHS N199A).

Flowers:

*Quantity per spadix*.—460 to 510.

*Spadix flower arrangement*.—Bisexual, rounded in cross-section.

*Shape*.—Rounded.

*Size*.—Length: 0.05 cm to 0.10 cm. Diameter (maximum): 0.10 cm.

*Color*.—RHS 158C.

Reproductive organs:

*Stamens*.—Not visible.

*Pollen amount*.—Absent.

*Pistil*.—Quantity: 450 to 500. Length: Less than 0.01 cm. Color: RHS 158C.

*Style*.—Not observed to date.

*Stigma*.—Shape: Ovoid. Diameter: Less than 0.01 cm. Color: RHS 158C.

*Ovary*.—Rarely visible.

*Ovary color*.—Not measured.

Fruit and seed set: Fruit and seed production has not been observed to date.

Disease and pest resistance: No specific resistance or susceptibility observed to pathogens or pests common to *Anthurium* under commercial conditions to date.

COMPARISON WITH PARENTAL AND SIMILAR COMMERCIAL VARIETIES

'AN2443227' differs from the female parent plant '06-008398-0002' (unpatented) in that 'AN2443227' has oblong-cordate spathes that are adpressed, basal part of the spadices are pink, and distal part of the spadices are reddish-brown, whereas '06-008398-0002' has orbicular-cordate spathes that are free, basal part of the spadices are white, and distal part of the spadices are green.

'AN2443227' differs from the male parent plant '03-006204-0001' (unpatented) in that 'AN2443227' has green spathes on the upper side that have strong blistering and the distal part of the spadices are reddish-brown, whereas '03-006204-0001' has white spathes on the upper side that have medium blistering and the distal part of the spadices are red.

'AN2443227' differs from the similar commercial variety 'ANTOSNA' (unpatented) in that 'AN2443227' has adpressed, red-tipped spathes and distal part of the spadices, before dehiscence of anthers, is reddish-brown, whereas the spathes of 'ANTOSNA' are incurved, but not touching, green-tipped spathes, and distal part of the spadices, before dehiscence of anthers, is green. Additionally, the curvature of longitudinal axis of 'AN2443227' is straight, whereas the curvature of longitudinal axis of 'ANTOSNA' is strongly incurved.

'AN2443227' differs from the similar commercial variety 'ANTHLINYJ' (unpatented) in that 'AN2443227' has adpressed, oblong-cordate spathes, and straight spadices, whereas 'ANTHLINYJ' has free, cordate spathes, and weakly incurved spadices.

I claim:

1. A new and distinct variety of *Anthurium* plant named 'AN2443227', substantially as illustrated and described herein.

* * * * *